(12) United States Patent
Briegel et al.

(10) Patent No.: US 8,044,238 B2
(45) Date of Patent: Oct. 25, 2011

(54) METHOD FOR PRODUCTION OF PURIFIED (METH)ACRYLIC ACID

(75) Inventors: Keith F. Briegel, Houston, TX (US); Michael Stanley DeCourcy, Houston, TX (US); James Elder, Houston, TX (US); James Jerrick Juliette, Houston, TX (US); Joy Lydon Mendoza, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 271 days.

(21) Appl. No.: 12/455,371

(22) Filed: Jun. 1, 2009

(65) Prior Publication Data

US 2009/0299090 A1    Dec. 3, 2009

Related U.S. Application Data

(60) Provisional application No. 61/130,347, filed on May 30, 2008.

(51) Int. Cl.
*C07C 51/42* (2006.01)
(52) U.S. Cl. .................................................. 562/600
(58) Field of Classification Search ....................... None
See application file for complete search history.

(56) References Cited

U.S. PATENT DOCUMENTS

| 2001/0016668 A1* | 8/2001 | Mitsumoto et al. ........... 562/600 |
| 2006/0142613 A1* | 6/2006 | Yada et al. .................... 562/600 |

* cited by examiner

*Primary Examiner* — Karl J Puttlitz
(74) *Attorney, Agent, or Firm* — Marcella M. Bodner (57) ABSTRACT

The present invention relates to reducing corrosion of distillation equipment during azeotropic distillation of (meth)acrylic acid in the presence of dissolved copper, by providing aqueous (meth)acrylic acid having not more than 0.1% by weight formaldehyde, based on the total weight of the aqueous (meth)acrylic acid. The source of the copper may, for example, be copper-based polymerization inhibitors added to the aqueous (meth)acrylic acid and/or distillation equipment.

10 Claims, 1 Drawing Sheet

METHOD FOR PRODUCTION OF PURIFIED (METH)ACRYLIC ACID

This invention claims priority to U.S. Provisional Application No. 61/130,347 filed May 30, 2008.

FIELD OF THE INVENTION

The present invention relates to purification by azeotropic distillation of (meth)acrylic acid from raw or aqueous (meth) acrylic acid.

BACKGROUND OF THE INVENTION

Monomers, such as unsaturated carboxylic acids and unsaturated nitrites, are industrially important as starting and intermediate materials for producing various synthetic resins, coating materials, fibers, plasticizers, synthetic resins, and the like. Commercially, there are various processes for producing unsaturated carboxylic acids (e.g., acrylic acid and methacrylic acid) and unsaturated nitrites (e.g., acrylonitrile and methacrylonitrile), but broadly, all such processes begin in essentially the same manner, via the catalytic reaction of one or more hydrocarbons to produce an impure gaseous material comprising the desired monomer. It is then necessary to recover the desired monomer from the impure gaseous material, and then to further purify it in order to minimize the amount of other materials, by-products, and impurities present in the recovered monomer stream.

For example, one well-known and commercially successful process for acrylic acid manufacture involves a two-step vapor phase catalytic oxidation reaction wherein propylene is converted first to acrolein in a first process step, and the acrolein is then converted to acrylic acid in a second process step. The resulting gaseous material stream comprises acrylic acid, but also water, unreacted propylene and acrolein, and several by-products including, but not limited to, one or more of the following compounds: formaldehyde, acetic acid, propionic acid, benzaldehyde, furfural, and maleic acid. Another known process which is currently being explored and developed is the single step vapor phase catalytic oxidation of propane in the presence of a suitable catalyst, and which also produces a gaseous material stream comprising acrylic acid, water, carbon oxides, unreacted propane, propylene, acrolein and several by-products including, but not limited to, one or more of the following compounds: formaldehyde, acetic acid, propionic acid, benzaldehyde, furfural, and maleic acid.

Regardless of the reaction process which produces it, aqueous acrylic acid is then most typically recovered from the raw gaseous product stream in an absorption tower, wherein a cooled absorbent, such as water or an organic compound (e.g., phenyl ether) directly contacts the gaseous material stream, simultaneously condensing and absorbing various components, including acrylic acid and water, from the gaseous material stream to produce an aqueous acrylic acid stream. This aqueous mixture typically contains appreciable amounts of by-products and impurities such as acrolein, formaldehyde, and water. This is, at least in part, because direct-contact absorption processes also capture by-products and impurities with the (meth)acrylic acid from the gaseous (meth)acrylic acid-containing material, rather than only the desired (meth)acrylic acid product. For this reason, it is common for the resulting aqueous acrylic acid stream to be subjected to one or more purification steps. The intended use for the acrylic acid will often determine the degree to which the material stream must be purified and the extent to which the other materials must be removed or separated from the acrylic acid.

Purification, or separation of the desired acrylic acid product from other materials in the aqueous acrylic acid stream may be accomplished by one or more well-known and understood processes including distillation, extraction, and/or crystallization. One of the most common of these purification steps is the use of azeotropic distillation to remove water from the aqueous acrylic acid stream. The purification of aqueous acrylic acid streams via azeotropic distillation is well known in the art of acrylic acid production. Various azeotropic distillation processes have been developed over the years based upon different azeotropic agents, for example U.S. Pat. No. 3,798,264 teaches the use of isobutyl acetate (IBAc) as the azeotropic agent, GB Patent No. 2146636 teaches the use of methyl isobutyl ketone (MIBK) as the azeotropic agent, and U.S. Pat. No. 6,399,817 teaches the use of toluene as the azeotropic agent.

Further purification processes, such as multiple distillation steps in series, or crystallization processes, are often necessary to meet final product quality requirements. Of course, each additional purification step requires additional initial capital investment, as well as higher operational costs.

For example, the process disclosed in U.S. Pat. No. 6,482,981 involves absorption of (meth)acrylic acid by direct contact of the material stream with water, followed by azeotropic distillation, and then by crystallization of the resulting aqueous acrylic acid to remove additional impurities and thereby minimize polymerization and formation of other solids. Such a complex process is therefore economically unattractive to construct and operate.

The prevention of polymer formation has also been a subject of great interest in the production of acrylic acid and many inhibitors have been identified for use at various points within the production process, including within the azeotropic distillation step. The large volume of prior art teaches that one or more inhibitors may be used, and that such inhibitors may include water soluble or alcohol soluble polymerization inhibitors. Polymerization inhibitors are typically used at levels ranging from 100 ppm to 4,000 ppm by weight. Particularly good polymer inhibition results have been achieved by using copper-based inhibitors, such as, for example one or more of copper dibutyldithiocarbamate (CB), copper dimethyldithiocarbamate, copper diethyldithiocarbamate, copper salicylate, copper naphthenate, and copper acetate, are added to the azeotropic distillation column. When such copper-based inhibitors are used along with a phenolic inhibitor, such as hydroquinone (HQ) or 4-methoxyphenol (MEHQ), the inhibition is improved even more.

It is important to note that some of the by-products and impurities in the aqueous acrylic acid stream may interfere with the operation and efficiency of downstream processes, such as further purification, storage, or reaction to produce other materials (e.g., esters of (meth)acrylic acids). For example, as explained in U.S. Patent Application Publication No. US 2007/0167650, high levels of formaldehyde in acrylic acid streams interact adversely with some polymerization inhibitors (e.g., phenothiazine ("PTZ"), hydroquinone ("HQ"), and monomethyl ether of hydroquinone (MeHQ")) resulting in formation of solid precipitates in the acrylic acid product. This reaction also reduces the effectiveness of the inhibitor molecules in preventing polymerization of the acrylic acid monomer, since some of the inhibitor is consumed in forming the solid precipitates. Further, these effects worsen with increasing temperatures, such as are often used in azeotropic distillation columns. It would therefore be advantageous to remove as much of these impurities as possible at the recovery step, prior to downstream purification of the aqueous acrylic acid. The disclosure of U.S. Patent Application Publication No. US 2007/0167650 fails to provide guidance for removing such impurities. Instead, the application only proposes that one limit, i.e., reduce, the concentration of inhibitors in the process to avoid the formation of precipitates. Such an approach is clearly at odds with reliable process operation, as it obtains reduced precipitate formation at the cost of insufficient process inhibition.

In particular, it has been witnessed that copper-based inhibitors have a tendency to be corrosive to the metallurgy of process equipment, such as azeotropic distillation columns and their associated equipment (e.g., condensers, piping, pumps, reboilers). This corrosive effect has been attributed to the formation of a galvanic corrosion cell wherein dissolved copper within the process liquid induces pitting of less noble metals, such as iron, aluminum, or zinc.

Various attempts to minimize the corrosive effects of copper based inhibitors have been proposed in the prior art. In particular, the prior art has been focused on identifying ways to mitigate the corrosive effects of copper dibutyl dithiocarbamate (CB) inhibitor. For example, U.S. Pat. No. 5,371,280 teaches that manganese can be added to the process in combination with CB inhibitor to mitigate corrosion. Similarly, U.S. Pat. No. 5,856,568 teaches the use of various additives including organic acids, to mitigate the corrosive effects of CB. Also, U.S. Patent Application Publication No. 2004/0011638 teaches the use of metal sequestering agents in combination with CB to mitigate corrosion. None of these solutions are completely satisfactory, however, because the corrosion was not totally eliminated and also because of the additional expense involved in purchasing such additives, as well as the need to remove these additional "impurities" from the product acrylic acid.

An alternative to the above mentioned use of additives, is to utilize metals that are highly resistant to corrosion as the materials of construction for azeotropic distillation columns and their associated equipment. One of ordinary skill in the art of corrosion engineering will easily recognize that metals which are more noble than copper in the Galvanic Series [see "Galvanic Series of Metals in Sea Water" from the Army Command Report RS-TR-67-11, (1967)] cannot undergo galvanic attack by dissolved copper within the process liquid. For example, noble metals such as zirconium, titanium, tantalum, or molybdenum would be good candidates for use as materials of construction for azeotropic distillation columns and their associated equipment. However, constructing process equipment with such noble metals is very expensive and industry would prefer to utilize lower-cost alloys, such as for example, nickel-chromium-iron alloys further comprising molybdenum, which are well known for their corrosion resistance, as the material of construction for azeotropic distillation columns and associated equipment. Two well-known examples of such alloys include 316L stainless steel (UNS S31603—comprising 2-to-3 mass % molybdenum) and 317L+ stainless steel (UNS S31725—comprising 4-to-5 mass % molybdenum).

In addition to lower cost, it is also taught in U.S. Pat. No. 6,441,228 that the use of nickel-chromium-iron alloys, with a molybdenum content of greater than 3 mass % to about 20 mass %, may provide the additional benefit of preventing polymer formation in (meth)acrylic acid production equipment.

Unfortunately, despite the presence of noble elements, such as molybdenum, in these alloys, such economic materials of construction have not performed in a consistent way with respect to corrosion resistance in azeotropic distillation systems. Further, despite the teachings of U.S. Pat. No. 6,441,228, applicants have found that significant polymer formation still occurs when nickel-chromium-iron alloys with a molybdenum content of greater than 3 to about 20 mass %, based on the total mass of the alloy, are used as the material of construction for azeotropic distillation columns and their associated equipment.

As an alternative to conventional absorption with water or organic absorbents, U.S. Pat. No. 6,646,161 describes a process for recovering (meth)acrylic acid from a hot gas containing (meth)acrylic acid and a high proportion of non-condensable constituents, by "fractional condensation" of the hot gas. The desired aqueous acrylic acid product (having greater than 95% by weight acrylic acid) exits from the side of the fractional condenser, while light ends (uncondensed components) exit from the top and the heavier impurities and by-products exit as a condensed liquid stream from the bottom. Thus, the process of U.S. Pat. No. 6,646,161 produces an aqueous acrylic acid product, and at least two by-product streams which must be handled separately. Optionally, a wastewater stream may be withdrawn from the side of the fractional condenser, further increasing the acrylic acid content of the aqueous acrylic acid side stream, but also creating a third by-product stream which must be processed. The fractional condenser used in this process is divided into "sections" to solve various engineering problems (i.e., separation of multiple components whose boiling points differ by greater than 25° C.) and accomplishes simultaneous cooling of the hot gas and condensation of the higher boiling fraction thereof. Thus, this process may be considered a combination of rectification and absorption which is often accomplished in to separate steps in conventional processes. The benefits of obtaining a purified acrylic acid stream from such a process are outweighed, however, by the substantial complexity of having multiple streams to process and the incremental capital cost of the additional process equipment required for such an operating approach.

Industry would welcome processes which produce aqueous acrylic acid with reduced corrosion of downstream process equipment, such as the corrosion of distillation equipment by compounds which are the products of copper-formaldehyde interactions. It is believed that the method of the present invention addresses these needs by providing an aqueous (meth)acrylic acid feed stream for the downstream purification processes which comprises less formaldehyde for interaction with copper present in the stream and derived from copper-based polymerization inhibitors.

SUMMARY OF THE INVENTION

The present invention provides a method for minimizing corrosion of apparatus during distillation of aqueous (meth) acrylic acid in the presence of dissolved copper. It has been found that dissolved copper interacts with formaldehyde to form formic acid, which is highly corrosive to distillation apparatus and related equipment. The method comprises: a) providing an aqueous acrylic acid feed stream comprising acrylic acid, water, and formaldehyde, wherein formaldehyde is present in an amount of not more than 0.1% by weight, based on the total weight of the aqueous acrylic acid stream; and b) purifying the aqueous acrylic acid feed stream by azeotropic distillation in the presence of dissolved copper. The gaseous material stream comprising acrylic acid may be derived from oxidizing at least one hydrocarbon, selected from the group consisting of propylene and propane, in a catalytic vapor-phase shell-and-tube reactor. The dissolved copper may, at least in part, be derived from the addition of copper-containing inhibitors to the aqueous acrylic acid stream during azeotropic distillation, the copper-containing inhibitors comprising one or more compounds selected from the group consisting of: copper dibutyldithiocarbamate (CB), copper dimethyldithiocarbamate, copper diethyldithiocarbamate, copper salicylate, copper naphthenate, and copper acetate.

Furthermore, the step of providing the aqueous acrylic acid may be accomplished by: 1) providing a gaseous material stream to a condenser, wherein the gaseous material stream comprises at least acrylic acid, water, acrolein, formaldehyde; and 2) operating the condenser and producing a gaseous vent stream comprising uncondensed components, and a condensed aqueous acrylic acid stream comprising acrylic acid.

In another embodiment, the method may further comprise, prior to performing purifying step b), stripping the aqueous acrylic acid stream in an acrolein removal column to obtain a reduced-acrolein content aqueous acrylic acid stream and a condensate stream comprising acrolein, wherein the condensate stream is recycled and provided to the condenser, and the reduced-acrolein content aqueous acrylic acid stream is the aqueous acrylic acid feed stream provided to the azeotropic distillation column.

BRIEF DESCRIPTION OF THE DRAWINGS

A more complete understanding of the present invention will be gained from the embodiments discussed hereinafter and with reference to the accompanying FIGURE which is a schematic representation of the method of the present invention.

DETAILED DESCRIPTION OF THE INVENTION

Figure 1:
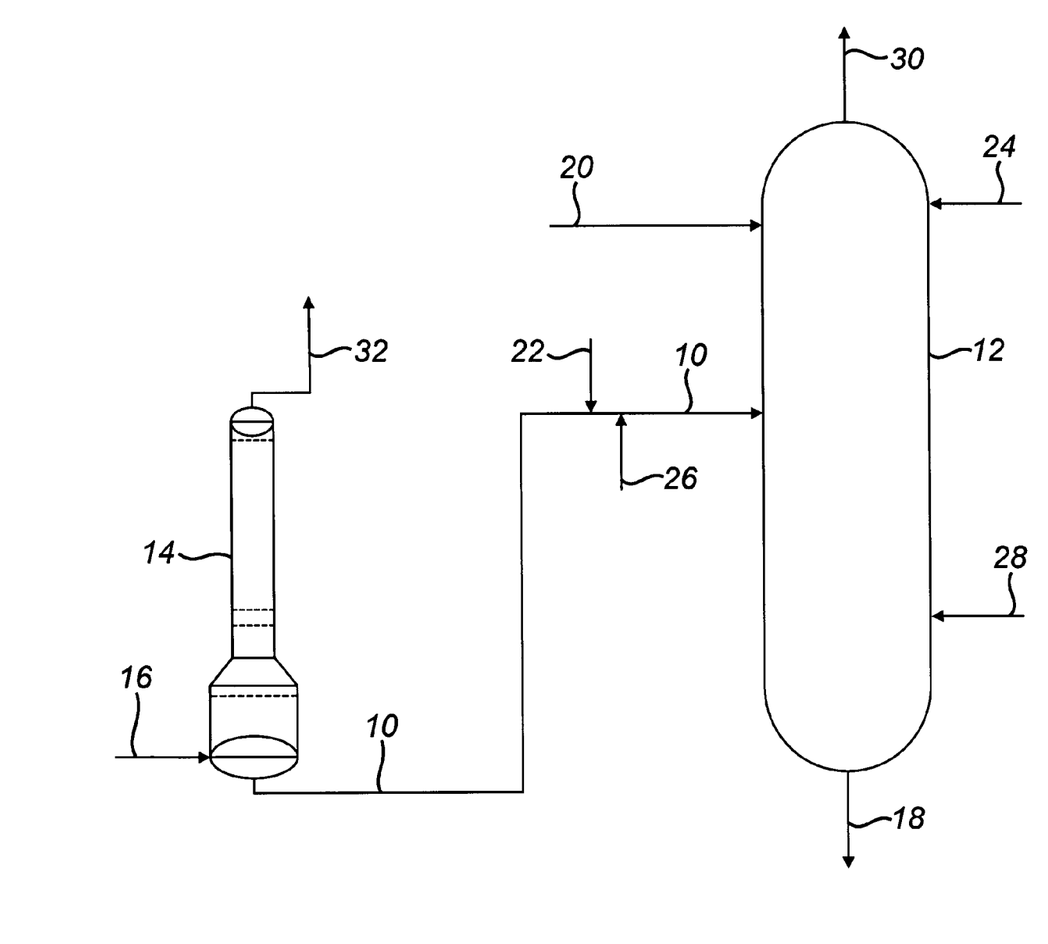

The following definitions and meanings are provided for clarity and will be used hereinafter.

As used herein, the term "$C_2$ to $C_4$ alkane" means a straight chain or branched chain alkane having from 2 to 4 carbons atoms per alkane molecule, for example, ethane, propane and butane, which are typically in the vapor phase at ordinary temperatures and pressures (e.g., at least 10° C. and 1 atmosphere). Similarly, the term "$C_2$ to $C_4$ alkene" means a straight chain or branched chain alkene having from 2 to 4 carbons atoms per alkene molecule, for example, ethene, propene and butene.

Endpoints of ranges are considered to be definite and are recognized to incorporate within their tolerance other values within the knowledge of persons of ordinary skill in the art, including, but not limited to, those which are insignificantly different from the respective endpoint as related to this invention (in other words, endpoints are to be construed to incorporate values "about" or "close" or "near" to each respective endpoint). The range and ratio limits, recited herein, are combinable. For example, if ranges of 1-20 and 5-15 are recited for a particular parameter, it is understood that ranges of 1-5, 1-15, 5-20, or 15-20 are also contemplated and encompassed thereby.

The method of the present invention produces an aqueous (meth)acrylic product having reduced quantities of impurities and by-products, particularly, less formaldehyde, than conventional processes by subjecting gaseous material streams comprising (meth)acrylic acid to a combination of one or more condensation steps using direct or indirect cooling with external heat exchangers and/or contact between the gaseous stream with the condensate in a column. The cooling obviates the need to add water, as is done in direct water-based absorption methods, which in turn minimizes the amount of formaldehyde that transfers from the gas phase into the aqueous (meth)acrylic acid. Further purifying steps, such as azeotropic distillation, non-azeotropic distillation, or crystallization, may be performed after the condensation, to remove additional water, by-products and impurities, as desired. Thus, the present invention provides a method for reducing solids formation (polymer and fouling material) during downstream processing of aqueous (meth)acrylic acid, for example during purification processes (e.g., in distillation columns, on trays/packing, within reboilers & piping), transport and storage of aqueous (meth)acrylic acid.

With reference now to the FIGURE, a schematic representation of the method of the present invention is provided wherein aqueous (meth)acrylic acid 10 is provided to a purification apparatus, such as a distillation column 12, in which it is subjected to azeotropic distillation. The aqueous (meth) acrylic acid 10 fed to the distillation column 12 comprises from 75% to 95%, by weight, (meth)acrylic acid and not more than 0.1%, by weight formaldehyde, based on the total weight of the aqueous (meth)acrylic acid 10. For example, without limitation, the aqueous (meth)acrylic acid 10 fed to the distillation column 12 may comprise not more than 0.05% by weight, or even not more than 0.01% by weight formaldehyde, based on the total weight of the material stream aqueous (meth)acrylic acid 10.

The aqueous (meth)acrylic acid 10 may further comprise additional by-products and impurities including, but not limited to, unreacted reactants and intermediate products, water, acrolein, acetic acid, propionic acid, maleic acid, maleic anhydride, other aldehydes and organics.

The aqueous (meth)acrylic acid 10 may already contain one or more polymerization inhibitors before it is provided to the distillation column 12. As is well known in the relevant art, such inhibitors may include water soluble or alcohol soluble polymerization inhibitors and are typically used at levels ranging from 100 ppm to 4,000 ppm by weight. Examples of inhibitors suitable for use in the production of acrylic acid, including within the azeotropic distillation step include but are not limited to: hydroquinone (HQ); 4-methoxyphenol (MEHQ); 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5-trimethylhydroquinone; 4-aminophenol; 2-aminophenol; 2-N,N-dimethylaminophenol; 2-mercaptophenol; 4-mercaptophenol; catechol monobutylether; 4-ethylaminophenol; 2,3-dihydroxyacetophenone; pyrogallol-1,2-dimethylether; 2-methylthiophenol; t-butyl catechol; di-tert-butylnitroxide; di-tert-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol; 4-nitrosophenol; copper dimethyldithiocarbamate; copper diethyldithiocarbamate; copper dibutyldithiocarbamate (CB); copper salicylate; methylene blue and salts thereof; iron; phenothiazine (PTZ); 3-oxophenothiazine; 5-oxophenothiazine; phenothiazine dimer; 1,4-benzenediamine; N-(1,4-dimethylpentyl)-N'-phenyl-1,4-benzenediamine; N-(1,3-dimethylbutyl)-N'-phenyl-1,4-benzenediamine; N-nitrosophenyl hydroxylamine and salts thereof; nitric oxide; nitrosobenzene; p-benzoquinone; copper naphthenate; copper acetate; manganese dimethyldithiocarbamate; manganese diethyldithiocarbamate; manganese dibutyldithiocarbamate; manganese naphthenate; manganese acetate; manganese acetylacetonate; cobalt acetate; cobalt carbonate; cobalt acetate; nitrogen dioxide; nitrobenzene; nitrosobutane; N-nitrosodiphenylamine; diphenylphenylenediamine; nitrosocarbazole; 1-nitroso-2-naphthol; 2,4 dinitrobenzene; triphenyl phosphine; triethyl phosphine; tributyl phosphine; triphenyl phosphite; triethyl phosphite; tri-i-propylphosphite; tributyl phosphite; tricyclohexyl phosphite; sodium bisulfite; butyl mercaptan; dodecyl mercaptan; N,N-diethylhydroxylamine; or isomers thereof; mixtures of two or more thereof; mixtures of one or more of the above with molecular oxygen. The inhibitor(s) may be used alone or combined with a suitable diluent or carrier, such as water, alcohol, or (meth)acrylic acid.

Of these inhibitors, copper-based inhibitors have been found to provide particularly good results when used to prevent polymerization in aqueous (meth)acrylic acid during distillation. For example one or more of copper dibutyldithiocarbamate (CB); copper dimethyldithiocarbamate; copper diethyldithiocarbamate; copper salicylate; copper naphthenate; and copper acetate may be added to the distillation column 12. For example, a combination of copper-based inhibitor and a phenolic inhibitor, such as hydroquinone (HQ) or 4-methoxyphenol (MEHQ), is known to be particularly beneficial. However, it is also known that copper-based inhibitors have a tendency to be corrosive to the metallurgy of process equipment, such as distillation columns 12 and their associated equipment (e.g., condensers, piping, pumps, reboilers (not shown per se)).

Attempts to mitigate and control this type of corrosion have met with variable success. Applicants have now, surprisingly, discovered that there is another, previously unidentified factor in the performance of materials of construction with respect to corrosion in the presence of dissolved copper. Without wishing to be bound by theory, it is now believed that formaldehyde interacts with the copper-based inhibitors to create formic acid which may form and concentrate within the azeotropic distillation column 12 of the acrylic acid production process. Furthermore, it is believed that the formic acid attacks and damages the passivation layer of materials such as stainless steels, making them susceptible to copper-induced pitting and galvanic attack.

In view of this heretofore unidentified root cause of this corrosion issue, the method of the present invention provides for minimizing formic acid within the azeotropic distillation columns 10 and their associated equipment, thereby allowing economical metallurgy to be utilized in the construction of azeotropic distillation systems, without concern for sudden, severe corrosion, such as copper-induced pitting. The method of the present invention allows such columns to be constructed of one or more metals selected from the list including 316 Stainless Steel (UNS31600), 316L Stainless Steel (UNS S31603), 317 Stainless Steel (UNS S31700), 317L+ Stainless Steel (UNS S31725 & S31726), Al6XN (UNS N08367), Inconel 625 (UNS N06625), 904L (UNS N08904), DUPLEX 2205 (UNS S31803), DUPLEX 2507 (UNS S32750), DUPLEX 2304 (UNS S32304), DUPLEX alloy 329 (UNS S32900), Alloy 20 CB-3 (UNS N08020), HASTELLOY C22 (UNS N06022), HASTELLOY C276 (UNS N10276), and HASTELLOY B2 (UNS N10665).

With reference back to the FIGURE, the aqueous (meth) acrylic acid 10 is provided to the distillation column 12 which comprises conventional internal apparati (e.g., trays, baffles, packing, etc.) and their associated equipment (e.g., condensers, piping, pumps, reboilers, etc.). One or more inhibitors 20, which comprise at least one copper-based inhibitor, are also provided to the distillation column 12, either directly 20, or indirectly by addition to an existing feed stream, such as the aqueous (meth)acrylic acid 10 being purified (see FIGURE, stream 22), prior to entry into the column 12. The inhibitors 20, 22 may be mixed with a diluent or carrier such as water or alcohol, if suitable, as known and understood in the art. Optionally, oxygen-containing gas 28 may also be added to the lower part of the column. An azeotroping agent, such as, without limitation, MIBK, or toluene, may be provided, directly or indirectly 24, 26, to the distillation column 12 for performing azeotropic distillation.

Purified aqueous (meth)acrylic acid 18 comprising from 90% to 99.8% by weight (meth)acrylic acid leaves the bottom of the distillation column 12. Low boiling point components (e.g., by-products and impurities) exit the top of the column 12 as "light ends" 30.

The source of the aqueous (meth)acrylic acid 10 is not critical, as long as the (meth)acrylic acid content is between about 60% and 95% by weight, and the formaldehyde content is not more than 0.1% by weight, such as 0.05% by weight, or even 0.01% by weight, based on the total weight of the aqueous (meth)acrylic acid 10. For example, without limitation, aqueous (meth)acrylic acid 10 may be the crude aqueous (meth)acrylic acid product from a separation apparatus 14, such as, without limitation, an absorber, a condenser, or a stripper (not shown per se), which separates (meth)acrylic acid product from the gaseous product stream 16 of a hydrocarbon oxidation reactor (not shown) wherein the hydrocarbon was a $C_2$ to $C_4$ alkane or alkene (i.e., ethane, propane, or butane, or ethylene, propylene, n-butylene or iso-butylene, respectively).

For example, where the separation apparatus 14 is a condenser, it may be used to perform one or more cooling steps, either direct cooling (such as heat exchanger) or indirect cooling (such as liquid pump around loop), and also allows for contacting of the condensate and gas streams in a conventional column with internals like trays, packing, etc. (not shown). Moreover, the condenser (separation apparatus 14) may be of various configurations, well-known to persons of ordinary skill in the relevant art, such as where cooling occurs only at the top of the condenser, or only at the bottom, or even throughout the condenser column, with multiple external loops. Moreover, the condenser or other separation apparatus 14 may be made of any suitable material including, but not limited to, 316 Stainless Steel (UNS31600), 316L Stainless Steel (UNS S31603), 317 Stainless Steel (UNS31700), 317L+ Stainless Steel (UNS S31725 & S31726), Al6XN (UNS N08367), Inconel 625 (UNS N06625), 904L (UNS N08904), Duplex 2205 (UNS S31803), Duplex 2507 (UNS S32750), Duplex 2304 (UNS S32304), Duplex alloy 329 (UNS S32900), Alloy 20 CB-3 (UNS N08020), and Hastelloy B2 (UNS N10665). Typically, the condenser column includes internal components such as distributors, baffles, solid packing materials, trays, etc., as necessary and determinable by persons of ordinary skill in the relevant art.

The aqueous (meth)acrylic acid 10 produced by upstream separation apparatus 14 has from 60% to 95% by weight, of (meth)acrylic acid, and not more than 0.1% by weight, of formaldehyde, such as, for example not more than 0.05%, or even not more than 0.01% by weight, based on the total weight of the aqueous (meth)acrylic acid. These lower formaldehyde levels in the aqueous (meth)acrylic acid 10 lessen the formation of polymer and other fouling solids (e.g., the reaction products of formaldehyde and phenolic inhibitors) in downstream process equipment, such as the azeotropic distillation column 12, as well as strippers, additional distillation columns, and crystallizers, which further yields higher asset utilization and lower operating cost. A vapor stream 32 of non-condensable materials exits from the top of the condenser 14.

The process and method of the present invention will be clarified by the following examples.

EXAMPLES

Example 1

A commercial-scale, MIBK-based azeotropic distillation column was used in a process of the type described in GB2146636 for the production of purified acrylic acid.

Specifically, the azeotropic distillation column was 141 inches (358 cm) in diameter and comprised 50 perforated plate trays without downcomers. As is common in the art, each tray was made up of 16 individual "panels", or strips, with a width sufficiently narrow (about 21 inches/53.34 centimeters) so as to easily pass through a standard column manway for installation and removal. To minimize fabrication cost, the azeotropic distillation column was bimetallic, comprising a lower section of 317L+ stainless steel (trays 1 through 21) and an upper section of 316L stainless steel (trays 22 through 50).

Standard corrosion-testing coupons were placed inside the column on Tray 23 to gain comparative performance data for 316L stainless steel vs. 317L+ stainless steel.

A mixture of hydroquinone (HQ) and copper dibutyldithiocarbamate (CB) inhibitors was added to the aqueous acrylic acid feed stream just prior to its delivery into the azeotropic distillation column to inhibit polymerization. Oxygen was also added to the bottom of the column. Additionally, a mixture of HQ and CB inhibitors was added to the reflux stream, prior to its return to tray 50 of the column.

The temperature at the bottom of the column was maintained at about 94° C. (201° F.); the top of the column was operated at a temperature of about 43° C. (109° F.) and a pressure of about 100 mmHg (13,332 Pa).

The column was operated for an extended period with an aqueous acrylic acid feed stream comprising about 65% acrylic acid supplied to the column on tray 28, and the column produced a purified bottoms product comprising about 93% acrylic acid by weight, based on the total weight of the bottoms product.

Inspection A (6 Months Operation)

The column was briefly shutdown and opened in order to retrieve the corrosion coupons for examination. At that time, the surface finish of Trays 14-21 (317L+ metallurgy) and Trays 22-24 (316L metallurgy) was noted to be rough and the mounting hardware for these trays showed visible signs of corrosion. From examination of the standard corrosion-testing coupons placed within the column, the corrosion rate, reported in standard corrosion units of mils-per-year (MPY), was found to be:

316L=3.5 mpy
317L+=0.6 mpy

Inspection B (27 Months Operation)

The column was shutdown and opened for inspection of the 316L section. Trays 22-25 (the "center of the column") were found to be thinning, indicating ongoing corrosion.

Inspection C (48 Months Operation)

The column was shutdown and opened for inspection of the center of the column. Thinning of Trays 22-26 was found to be ongoing and some of the mounting hardware for these trays was sufficiently corroded so as to require immediate replacement. Additionally, some of the panels within Tray 24 were found to be significantly corroded and were replaced. Due to production demands, the column was quickly returned to service, but planning was initiated for a more rigorous inspection of the column.

Inspection D (52 Months Operation)

The column was shutdown and opened for a complete inspection. Substantial polymer accumulation (3-5 inches in depth) was discovered upon Trays 1-10 (317L+ metallurgy).

An additional panel within tray 24 (not previously replaced) was now found to be significantly corroded and was replaced. Severe pitting of the interior surfaces of the column shell was discovered at the center of the column and it was recommended that the column shell and trays between trays 20 and 30 be replaced due to their deteriorating condition.

Inspection E (54 Months Operation)

The column was again shutdown and opened for inspection. Substantial polymer accumulation was discovered upon trays 1-7 and also trays 19-21 (all 317L+ metallurgy).

Ongoing corrosion is evident in the center of the column.

Inspection F (62 Months Operation)

The column was shutdown for repairs. Because of the severity of the damage, in-place repairs were determined to be uneconomical; instead, a new 17-tray section of column was fabricated from 317L+ Stainless Steel, the column section between trays 21-39 was cut-out and removed, and the new 317L+ SS section was welded into place to return the column to serviceable condition. Before returning the column to service, the lower (317L+) portion of the column was inspected; it was discovered the column shell, trays, and tray hardware from trays 15 to 21 were suffering from corrosive attack and would require ongoing monitoring.

Inspection G (67 Months Operation)

The column was briefly shutdown and opened in order to remove polymer from trays 1 through 10 (317L+ metallurgy).

Inspection H (77 Months Operation)

The column was again shutdown and opened for inspection. Substantial polymer accumulation was discovered upon trays 5 through 16 (317L+ metallurgy). Despite the upgraded metallurgy at the center of the column, etching-type corrosion of the new 317L+ trays 21 to 30 was detected.

Inspection I (86 Months Operation)

The column was shutdown and opened for a complete inspection. Substantial polymer accumulation was discovered upon trays 1-4, with somewhat lighter accumulation on trays 5-10 (317L+ metallurgy). Ultrasonic thickness (UT) measurements of the column shell in the center of the column indicates a maximum loss rate of 0.032 inch per year (32 mpy). Metallurgical inspection results were as follows:

Trays 28-50=no corrosion

Trays 22-27=significant corrosion; one-fourth of each tray (about 4 panels) in this region was replaced with a new panels made from Hastelloy C276; mounting hardware for these trays was also visibly corroded.

Trays 20 & 21=extreme corrosion; Holes up to 12 inches in diameter have formed in these trays; one-half of each tray (about eight panels) in this region was replaced with new panels made from Hastelloy C276; mounting hardware for these trays was visibly corroded.

The corrosion discovered during this inspection is especially surprising given that that the original Trays 20-27 were all replaced with new 317L+ trays during repairs made just 24 months before this inspection.

Trays 16-19=moderate metal loss; mounting hardware for these trays was visibly corroded.

Trays 13-15=no tray deterioration detected; mounting hardware for these trays was visibly corroded.
Trays 1-12=no corrosion
Inspection J (96 Months Operation)

The column was shutdown and opened for a complete inspection. Polymer accumulation was found upon all trays from tray 1 through tray 24 (317L+ and some Hastelloy C276 metallurgy). Metallurgical Inspection results were as follows:
Trays 41-50=no corrosion (all 316L metallurgy)
Trays 38-40=etching on trays and column shell (all 316L metallurgy)
Trays 31-37=minimal evidence of corrosion (all 317L+ metallurgy)
Trays 29 & 30=etching on bottom surface of trays (317L+ metallurgy)
Trays 14-28=Severe etching and moderate metal loss to 317L+ portions of trays/HASTELLOY C276 tray panels in trays 20-27 were free of corrosion; visible corrosion of mounting hardware and column shell (317L+ metallurgy), with area of greatest shell damage located between Trays 16-20.
Trays 1-13=no corrosion detected (all 317L+ metallurgy)

Example 2

Additional studies were performed using corrosion-testing coupons under actual process conditions in an attempt to identify suitable materials of construction for this service.

In these studies, two sets of corrosion coupons were sequentially placed on tray 15, within the azeotropic distillation column of example 1, and then removed and examined to determine the corrosion rate of each material. The results from each set of corrosion-testing coupons are shown below, with corrosion rates reported in standard corrosion units of mils-per-year (MPY or milli-inch per year).

| Example 2a - first set | | |
|---|---|---|
| Material Name | Material UNS # | Corrosion rate (MPY) |
| 316L | S31603 | 8.8 |
| 317L | S31703 | 2.4 |
| 317LM | S31725 | 2.2 |
| 904L | N08904 | 3.4 |
| AL6XN | N08367 | 0.1 |
| HASTELLOY C276 | 10276 | 0.0 |
| Duplex 2205 | S31803 | 1.6 |

| Example 2b - second set | | |
|---|---|---|
| Material Name | Material UNS # | Corrosion rate (MPY) |
| 304L | S30403 | 37.1 |
| 316L | S31603 | 7.1 |
| 317L | S31703 | 1.1 |
| 317LM | S31725 | 0.1 |
| AL6XN | N08367 | 0.0 |
| Duplex 2507 | S32750 | 0.0 |
| Duplex 2205 | S31803 | 0.2 |
| HASTELLOY C276 | 10276 | 0.0 |
| 904L | N08904 | 2.0 |
| HASTELLOY C22 | N06022 | 0.0 |

Metallurgical investigation of corroded components from the aforementioned examples identified the presence of copper within the pitted surface of the damaged 316L stainless steel and 317L+ stainless steel components. This in itself was surprising, because both the 316L SS alloy and the 317L+ SS alloy are expected to be more electrochemically noble than copper and so should not have been susceptible to galvanic attack by copper, especially at the lower operating temperature within the upper portion of the distillation column. After significant studies of the system, however, a previously unidentified, complex corrosion process was discovered, namely, that this corrosion process is initiated by concentrated formic acid attack of the column metallurgy. This was especially surprising because the presence of even low levels of formic acid within the process was unexpected.

Without being bound to theory, we currently understand this complex corrosion process to involve the following steps:
1) formaldehyde present in the aqueous acrylic acid feed stream is converted into formic acid within the distillation column; this conversion is catalyzed by dissolved copper within the distillation column process fluid
2) once formed, the formic acid concentrates in the upper part of the distillation column, where is attacks the 316L and 317L+ stainless steel components of the column, thereby damaging the passivation layer on these components
3) once the passivation layer is compromised, a galvanic corrosion cell is established between the dissolved copper in the process fluid and the 316L/317L+ stainless steel, leading to extensive copper-induced pitting of these stainless steel components
4) because a portion of the water removed in the distillation column of the example system is recycled back to the absorber, formic acid begins to accumulate in the absorber as well and eventually reaches a low-level steady state concentration in the aqueous acrylic acid feed stream Subsequent analyses of the steady state aqueous acrylic acid feed stream verified the presence of both formaldehyde and formic acid, as follows:

| | Sample #1 | Sample #2 | Sample #3 | range |
|---|---|---|---|---|
| Formaldehyde | 0.69% | 0.75% | 0.89% | 0.69-0.89% |
| Formic acid | 0.371% | 0.459% | 0.340% | 0.34-0.46% |

Thus, minimization of the amount of formaldehyde in the aqueous (meth)acrylic acid entering the azeotropic distillation column, when the polymerization inhibitors used include copper-based inhibitors, such as CB, should reduce and minimize apparatus corrosion of the type described above.

Example 3

Aqueous (Meth)Acrylic Acid Source

The following are examples of aqueous (meth)acrylic acid suitable for use in connection with the method of the present invention and which are produced by condensation of the gaseous product stream of a hydrocarbon (propylene) oxidation reactor. The following description are based on a combination of actual commercial-process data and computer models capable of predicting process results based on known equipment specifications and known operational data. The computer model used by applicants is commercially known as Aspen plus 2004.1 Simulation Engine and is available from Aspen Technology, located in Burlington, Mass., U.S.A.

Apparatus Specifications and General Operation

The equipment consists of a condenser which is a 316L stainless steel column with a 10-foot 6-inch (3.200 meters) diameter top section that is 102-feet 3-inches (31.166 meters) long, a 4-foot 4-inch (1.321 meters) long conical transition section, and a 15-foot 6-inch (4.724 meters) diameter by 30-foot 4-inch (9.246 meters) long bottom section. The top of the condenser column is equipped with a 11,832 square foot (1099 square meters) tubular exchanger, top cooler, providing up to 33 MM BTU/h (9.66 MW) cooling using 31° C. (88° F.) cooling water to cool the gas leaving the top of the column, and a separation vessel is designed to separate the vapor and liquid and collect the condensate for return to the top of the column by pump. The bottom section of the column has an external liquid pump around loop to provide cooling for the reactor exit gas, and consists of a 1100 gpm (250 m$^3$/h) pump drawing liquid from the bottom of the column, a 2807 square foot (261 square meters), 316L stainless steel tubular heat exchanger providing up to 30 MM BTU/h (8.78 MW) cooling using 31° C. (88° F.) cooling tower water, and return of the pump around liquid stream back to the bottom section above the packed bed described below.

Reactor exit gas is introduced to the condenser column at the lower portion of the bottom section, and then passes through a V-grid vapor distributor followed by a 10-foot (3.048 meter) deep bed of 316 stainless steel #4 cascade mini rings, all contained in the large diameter bottom section. The gas then moves up the column via the transition section and passes in series through two 23-foot (7.010 meters) deep beds of 316 stainless steel #3 cascade mini rings, followed by two 14-foot 4-inch (4.369 meters) deep beds of 316 stainless steel Sulzer BX structured packing. The gas leaves the top bed, exits the top of the column, and is then piped to the top cooler. After being cooled, the gas stream then passes through the separator to remove liquid condensate before leaving the system as 'off gas', and a portion is recycled to the feed of the reactor while the remainder is sent to a thermal oxidizer. The condensate collected by the separator vessel is feed to the top of the column and distributed to the top bed using a 316 stainless steel Nutter MTS-109 liquid distributor. After the liquid passes through each bed in the top section, the liquid is collected with a 316 stainless steel Nutter CFT-1206 chimney tray and redistributed to the next bed with a 316 stainless steel MTS-109 liquid distributor. Liquid leaving the top section is added to liquid from the pump around circulation loop and distributed to the bottom bed with a 316 stainless steel Nutter HLT-538 liquid distributor. As liquid accumulates in the bottom, sump, of the column it is drawn via pump from the system by level control. The liquid leaving the bottom of the condenser column is referred to as aqueous acrylic acid. The aqueous acrylic acid may be sent to downstream processes for further purification or, optionally, may be sent to an integrated acrolein removal column for efficient removal of acrolein.

In the embodiment of this example, the optional integrated acrolein removal column is utilized. The integrated acrolein removal column is a 4-foot 9-inch (1.448 meters) diameter, 304L stainless steel column with a 21-foot 8-inch (6.604 meters) packed bed of 304 stainless steel #2 cascade mini rings and is equipped with a 411 square foot (38.2 square meter) 304L stainless steel thermosyphon reboiler, a 949 square foot (88.2 square meter) 304L stainless steel main condenser and a 293 square foot (27.2 square meters), 304L stainless steel vent condenser. The condenser column bottoms material is feed at the top of the acrolein removal column, which is operated at about 200 mmHg (26,664 Pa) absolute pressure, passes through the packing and is then heated at the bottom of the column by the reboiler to vaporize about 5-10% by weight of the stream. The vapor exiting the reboiler passes through the packed bed to provide stripping and is then condensed by the main and vent condensers. The condensate, which comprises acrolein, is returned to the bottom section of the condenser column by addition to the return line for the pump around stream. By introducing the condensate in this manner, the acrolein is allowed to re-vaporize within the condenser column. The liquid exiting the bottom of the acrolein removal column is referred to as reduced acrolein content aqueous acrylic acid and is sent to downstream processes for further purification.

Example 3A

Actual Modeled Operation and Performance ("Medium Aqueous Strength")

Based on the above-described condenser equipment, operation of the inventive condenser system was simulated using the following reactor exit gas composition:

| Reactor Exit Gas Composition A | |
|---|---|
| Component | vol % |
| Nitrogen | 70.9% |
| Water | 16.8% |
| Acrylic Acid | 6.87% |
| Oxygen | 1.80% |
| Carbon Dioxide | 1.45% |
| Carbon Monoxide | 0.723% |
| Propane | 0.548% |
| Propylene | 0.245% |
| Acrolein | 0.104% |
| Acetic Acid | 0.274% |
| Formaldehyde | 0.224% |
| Maleic Acid | 0.0452% |
| Acetaldehyde | 0.0154% |
| Acetone | 0.0031% |

Reactor exit gas enters the bottom of the condenser column at a mass flowrate of 253,641 lb/h (115,050 kg/h), a temperature of 290° C. (554° F.), and a pressure of 7.3 psig (151,657 Pa).

The model was run with sufficient cooling at the bottom section of the condenser column to control the column top temperature at 68° C. (154° F.), and 25.7 MM BTU/h (7.53 MW) of cooling through the top cooler, resulting in a bottom temperature of 80.7° C. (177° F.). The off gas exiting the top of the vapor-liquid separator after the top cooler is calculated to be flowing at 200,421 lb/h (90,910 kg/h), at a pressure of 1.5 psig (111,667), and the model predicts the following composition:

| Off Gas Composition A | |
|---|---|
| Component | vol % |
| Nitrogen | 82.4% |
| Water | 11.5% |
| Acrylic Acid | 0.199% |
| Oxygen | 2.09% |
| Carbon Dioxide | 1.68% |
| Carbon Monoxide | 0.840% |
| Propane | 0.636% |
| Propylene | 0.285% |
| Acrolein | 0.119% |
| Acetic Acid | 0.0067% |

-continued

| Off Gas Composition A | |
|---|---|
| Component | vol % |
| Formaldehyde | 0.262% |
| Maleic Acid | 0% |
| Acetaldehyde | 0.0179% |
| Acetone | 0.0035% |

For the purpose of polymer inhibition, the column is provided with a 400 lb/h (181 kg/h) feed of de-ionized water with 5% by weight of hydroquinone (HQ) inhibitor. Aqueous acrylic acid exits the bottom of the condenser column at a flowrate of 58,176 lb/h (26,388 kg/h) and with the following composition:

| Aqueous Acrylic Acid Composition A | | | |
|---|---|---|---|
| Component | wt % | lb/h | kg/hr |
| Acrylic Acid | 74.5% | 43,317 | 19,690 |
| Water | 21.8% | 12,697 | 5,772 |
| Formaldehyde | 0.0228% | 13 | 6 |
| Acrolein | 0.0414% | 24 | 11 |
| Maleic Acid | 0.785% | 457 | 208 |
| Acetic Acid | 2.53% | 1,471 | 669 |
| Acetaldehyde | 0.0022% | 1 | 1 |

Per the simulation, the aqueous Acrylic acid stream of this example is then fed to the acrolein removal column, wherein acrolein is stripped and recycled to the condenser column. Reduced-acrolein content aqueous acrylic acid will be removed from the bottom of the acrolein removal column at a flowrate of 53,620 lb/h (24,322 kg/h) and will have the following composition:

| Reduced-Acrolein content Aqueous Acrylic Acid Composition A | | | |
|---|---|---|---|
| Component | w % | lb/h | kg/hr |
| Acrylic Acid | 76.2% | 40,858 | 18,572 |
| Water | 20.4% | 10,938 | 4,972 |
| Formaldehyde | 0.0003% | 0.2 | 0.1 |
| Acrolein | 0.0121% | 6 | 3 |
| Maleic Acid | 0.829% | 445 | 202 |
| Acetic Acid | 2.55% | 1,367 | 622 |
| Acetaldehyde | 0% | — | — |

Under the conditions of this example, it is clear that the method of the present invention provides significantly lower formaldehyde levels in aqueous acrylic acid than prior-art absorption processes, and that this benefit is maintained even when aqueous acrylic acid is stripped in an acrolein removal column.

Example 3B

Actual Operation and Performance ("High Aqueous Strength")

Based on the above-described condenser equipment, operation of the inventive condenser system was again simulated with the same reactor exit gas composition and mass flowrate (253,641 lb/h (115,050 kg/h)) as that used in Comparative Example 3A. In this example, the reactor exit gas is introduced to the bottom of the condenser column at a temperature of 290° C. (554° F.) and a pressure of 7.3 psig (151,657 Pa).

The model was run with no cooling in the bottom section of the condenser column and the top cooler is simulated to provide 43.5 MM BTU/h (12.7 MW) resulting in a 60° C. (140° F.) top cooler exit temperature and 103° C. (217° F.) column bottom temperature. The off gas exiting the top of the vapor-liquid separator after the top cooler is calculated to be flowing at 211,611 lb/h, (95,985 kg/h) at a pressure of 1.5 psig (111,667 Pa) and the model predicts the following composition:

| Off Gas Composition B | |
|---|---|
| Component | vol % |
| Nitrogen | 76.3% |
| Water | 17.9% |
| Acrylic Acid | 0.285% |
| Oxygen | 1.93% |
| Carbon Dioxide | 1.56% |
| Carbon Monoxide | 0.778% |
| Propane | 0.589% |
| Propylene | 0.264% |
| Acrolein | 0.110% |
| Acetic Acid | 0.0842% |
| Formaldehyde | 0.243% |
| Maleic Acid | 0% |
| Acetaldehyde | 0.0165% |
| Acetone | 0.0033% |

For the purpose of polymer inhibition, the column is provided with a 400 lb/h (181 kg/h) feed of de-ionized water with 5% by weight hydroquinone (HQ) inhibitor. Aqueous acrylic acid exits the bottom of the condenser column at a flowrate of 46,856 lb/h (21,254 kg/h) and with the following composition:

| Aqueous Acrylic Acid Composition B | | | |
|---|---|---|---|
| Component | wt % | lb/h | kg/hr |
| Acrylic Acid | 94.2% | 44,152 | 20,069 |
| Water | 2.19% | 1,026 | 466 |
| Formaldehyde | 0.0058% | 3 | 1 |
| Acrolein | 0.0304% | 14 | 6 |
| Maleic Acid | 0.982% | 460 | 209 |
| Acetic Acid | 2.45% | 1,147 | 521 |
| Acetaldehyde | 0.0014% | 1 | 0 |

Per the simulation, the aqueous Acrylic acid stream of this example is then fed to the acrolein removal column, wherein acrolein is stripped and recycled to the condenser column. Reduced-acrolein content aqueous acrylic acid will be removed from the bottom of the acrolein removal column at a flowrate of 42,430 (19,246 kg/h) lb/h and will have the following composition:

| Reduced-Acrolein content Aqueous Acrylic Acid Composition B | | | |
|---|---|---|---|
| Component | wt % | lb/h | kg/hr |
| Acrylic Acid | 95.0% | 40,309 | 18,322 |
| Water | 1.59% | 675 | 307 |
| Formaldehyde | 0.0012% | 0.5 | 0.2 |

-continued

Reduced-Acrolein content
Aqueous Acrylic Acid Composition B

| Component | wt % | lb/h | kg/hr |
|---|---|---|---|
| Acrolein | 0.0196% | 8 | 4 |
| Maleic Acid | 1.05% | 446 | 203 |
| Acetic Acid | 2.35% | 997 | 453 |
| Acetaldehyde | 0.0006% | 0 | 0 |

Under the conditions of this example, it is clear that the method of the present invention provides significantly lower formaldehyde levels in aqueous acrylic acid than prior-art absorption processes, and that this benefit is maintained even when aqueous acrylic acid is stripped in an acrolein removal column.

We claim:

1. A method for minimizing corrosion of apparatus during distillation of aqueous (meth)acrylic acid in the presence of dissolved copper, comprising:
   a) providing an aqueous acrylic acid feed stream comprising acrylic acid, water, and formaldehyde, wherein formaldehyde is present in an amount of not more than 0.1% by weight, based on the total weight of the aqueous acrylic acid stream; and
   b) purifying the aqueous acrylic acid feed stream by azeotropic distillation in the presence of dissolved copper.

2. The method of claim 1, wherein the aqueous acrylic acid feed stream comprises not more than 0.05% by weight formaldehyde.

3. The method of claim 1, wherein the aqueous acrylic acid feed stream comprises not more than 0.01% by weight formaldehyde.

4. The method of claim 1, wherein step a) is accomplished by
   1) providing a gaseous material stream to a condenser, wherein the gaseous material stream comprises at least acrylic acid, water, acrolein, formaldehyde; and
   2) operating the condenser and producing a gaseous vent stream comprising uncondensed components, and a condensed aqueous acrylic acid stream comprising acrylic acid, wherein the aqueous acrylic acid stream comprises not more than 0.1% by weight formaldehyde, based on the total weight of the aqueous acrylic acid stream, and wherein the balance of the formaldehyde originally in the gaseous material stream is contained in the gaseous vent stream.

5. The method of claim 4, wherein, prior to performing purifying step b), the aqueous acrylic acid stream is stripped in an acrolein removal column to obtain a reduced-acrolein content aqueous acrylic acid stream and a condensate stream comprising acrolein, wherein the condensate stream is recycled and provided to the condenser, and the reduced-acrolein content aqueous acrylic acid stream is the aqueous acrylic acid feed stream provided to the azeotropic distillation column.

6. The method of claim 4, wherein said step a) 1) of providing a gaseous material stream comprising acrylic acid is accomplished by oxidizing at least one hydrocarbon, selected from the group consisting of propylene and propane, in a catalytic vapor-phase shell-and-tube reactor to produce the gaseous material stream.

7. The method of claim 1, wherein the dissolved copper is at least in part, derived from the addition of copper-containing inhibitors to the aqueous acrylic acid stream during azeotropic distillation, the copper-containing inhibitors comprising one or more compounds selected from the group consisting of: copper dibutyldithiocarbamate (CB), copper dimethyldithiocarbamate, copper diethyldithiocarbamate, copper salicylate, copper naphthenate, and copper acetate.

8. The method of claim 1, wherein the azeotropic distillation is performed in a column constructed from one or more types of stainless steel selected from the group consisting of: 316SS, 316LSS, 317SS, 317L+SS, Al6XN, Inconel 625, 904L, Duplex 2205, Duplex 2507, Duplex 2304, Duplex alloy 329, Alloy 20 CB-3, Hastelloy C22, Hastelloy C276 and Hastelloy B2.

9. The method of claim 1, wherein the aqueous acrylic acid stream comprises between 75% and 95% by weight acrylic acid, based on the total weight of the aqueous acrylic acid stream.

10. The method of claim 1, wherein the gaseous stream further comprises non-condensable materials which have a boiling point, at atmospheric pressure, of no greater than −40° C.

* * * * *